(12) United States Patent
Chewter et al.

(10) Patent No.: US 8,822,709 B2
(45) Date of Patent: Sep. 2, 2014

(54) PROCESS FOR PREPARING AN EPOXIDE FROM AN OXYGENATE

(71) Applicant: Shell Oil Company, Houston, TX (US)

(72) Inventors: Leslie Andrew Chewter, Amsterdam (NL); Hervé Henry, Rotterdam (NL); Pieter Oldenhove, Amsterdam (NL); Rajaram Ramesh, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/653,135

(22) Filed: Oct. 16, 2012

(65) Prior Publication Data

US 2013/0096329 A1    Apr. 18, 2013

(30) Foreign Application Priority Data

Oct. 17, 2011  (EP) .................................... 11185489

(51) Int. Cl.
  *C07D 301/03*  (2006.01)
  *C07D 301/19*  (2006.01)
(52) U.S. Cl.
  CPC ................................... *C07D 301/19* (2013.01)
  USPC ...................................................... 549/523
(58) Field of Classification Search
  USPC ...................................................... 549/523
  See application file for complete search history.

(56) References Cited

U.S. PATENT DOCUMENTS

| 3,351,635 A | 11/1967 | Kollar ........................ 260/348.5 |
| 5,210,354 A | 5/1993 | Dubner et al. ................ 585/469 |
| 2005/0250969 A1 | 11/2005 | Bridges |
| 2006/0135833 A1 | 6/2006 | Malzkorn et al. |
| 2009/0105429 A1 | 4/2009 | Chewter et al. |
| 2011/0118523 A1 | 5/2011 | Winterberg et al. |

FOREIGN PATENT DOCUMENTS

| RU | 2197460 C1 | 1/2003 | |
| WO | 2009065898 A1 | 5/2009 | |
| WO | WO2009065848 | 5/2009 | ................ B01J 8/18 |
| WO | WO2009120290 | 10/2009 | ........... C07D 301/06 |

OTHER PUBLICATIONS

Chauvel, A., et al., "Petrochemical Processes—Part 1. Synthesis-Gas Derivatives and Major Hydrocarbon", Editions Technip, 1989, pp. 213-215.
Fields, D.L., et al., "Catalytic Destruction of Methyl Tertiary Butyl Ether (MTBE) with Pt/Rh Monolithic Automotive Exhaust Catalyst"; Applied Catalysis B: Environmental 15; 1998, pp. 93-15.
PCT International Search Report dated Jan. 25, 2013, Application No. PCT/EP2012/070517 filed Oct. 16, 2012.

*Primary Examiner* — T. Victor Oh

(57) ABSTRACT

The invention relates to an integrated process for preparing an epoxide from an oxygenate, wherein the oxygenate is converted into a lower olefin and the lower olefin is subsequently epoxidised, and wherein isobutane obtained after hydrogenation and subsequent normal/iso separation of C4 hydrocarbons obtained as by-product of the oxygenate conversion, is converted into a hydroperoxide that is used for the conversion of the lower olefin into the corresponding epoxide.

13 Claims, 2 Drawing Sheets

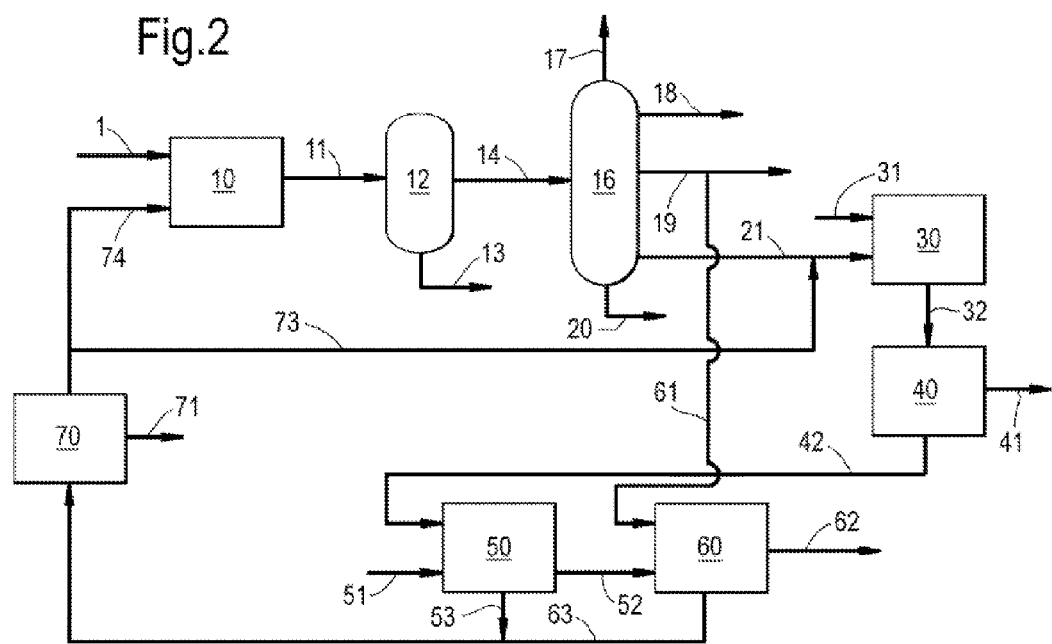

PROCESS FOR PREPARING AN EPOXIDE FROM AN OXYGENATE

This application claims the benefit of European Application No. 11185489.9 filed Oct. 17, 2011, which is incorporated herein by reference.

FIELD OF THE INVENTION

The invention relates to a process for preparing an epoxide from an oxygenate.

BACKGROUND TO THE INVENTION

Epoxides such as ethylene oxide and propylene oxide are important chemical intermediates. Propylene oxide is for example used as raw material for the production of polyether polyols, propylene glycol and glycol ethers. Ethylene oxide is for example used as raw material for the production of ethylene glycol, ethanolamines and acrylonitrile.

Epoxides are produced by epoxidation of olefins. Ethylene oxide is typically manufactured by direct oxidation of ethylene with oxygen. For propylene oxide, direct oxidation of propylene with oxygen has been proposed, for example in WO2009/120290. In practice, however, propylene is typically epoxidized to propylene oxide by reacting the propylene with an organic hydroperoxide, for example ethyl benzene hydroperoxide, tertiary butylhydroperoxide or cumene hydroperoxide. This is for example described in U.S. Pat. No. 3,351,635. An example of a commercially available epoxidation process that uses a hydroperoxide is the so-called SMPO process (Styrene Monomer Propylene Oxide process) wherein an ethyl benzene hydroperoxide is reacted with propylene to form methyl phenyl carbinol and propylene oxide. Methyl phenyl carbinol is subsequently dehydrated to styrene. Such process is for example disclosed in U.S. Pat. No. 5,210,354.

Conventionally, lower olefins such as ethylene and propylene are produced via steam cracking of hydrocarbon feedstocks including ethane, propane, naphtha, gasoil and hydrowax. An alternative route to lower olefins is the so-called oxygenate-to-olefin process. In such oxygenate-to-olefin process, an oxygenate such as methanol or dimethylether (DME) is provided to a reaction zone containing a suitable oxygenate conversion catalyst, typically a molecular sieve-comprising catalyst, and converted into ethylene and propylene. In addition to the desired lower olefins, a substantial part of the oxygenate is converted into C4+ olefins and paraffins.

In WO2009/065848 is disclosed an oxygenate-to-olefin process wherein the yield of lower olefins is increased by recycling a fraction comprising C4+ olefins to the reaction zone. At least part of the C4+ olefins in the recycle are converted into the desired lower olefins. A disadvantage of the process of WO2009/065848 is, however, that at least part of the recycle stream needs to be purged in order to avoid undesired accumulation of paraffins in the recycle stream. With the purge, also valuable C4+ olefins will be removed from the process without being converted into lower olefins.

Another disadvantage is that in an oxygenate-to-olefin process, less benzene is formed than in for example steam cracking of naphtha. If the lower olefins formed would then be converted into propylene oxide by an SMPO process, additional benzene would need to be imported and fed to the SMPO process.

SUMMARY OF THE INVENTION

It has now been found that the production of lower olefins from oxygenate and the subsequent epoxidation of the lower olefins can be advantageously integrated by converting iso-C4 hydrocarbons, which are co-produced in the conversion of oxygenate into lower olefins, into tertiary butyl hydroperoxide that is subsequently used for the conversion of the lower olefins into the corresponding epoxides.

Accordingly, the present invention relates to a process for preparing an epoxide from an oxygenate, the process comprising the following steps:

a) contacting the oxygenate with a molecular sieve-comprising catalyst, at a temperature in the range of from 350 to 1000° C. to obtain an olefinic product stream comprising ethylene, propylene and C4 hydrocarbons;

b) separating ethylene and/or propylene and a fraction comprising C4 hydrocarbons including normal butane, isobutane, normal butene and isobutene, from the olefinic product stream;

c) hydrogenating at least part of the fraction comprising C4 hydrocarbons in a hydrogenation unit to obtain a saturated C4 hydrocarbon stream;

d) separating the saturated C4 hydrocarbon stream into a stream enriched in normal butane and a stream enriched in isobutane;

e) oxidizing the isobutane in the stream enriched in isobutane into tertiary butyl hydroperoxide; and f) reacting tertiary butyl hydroperoxide obtained in step d) with ethylene and/or propylene separated from the olefinic product stream obtained in step a) to obtain the epoxide and tertiary butanol.

Thus, iso-C4 hydrocarbons, i.e. isobutane and isobutene, produced as by-product or intermediate product of the manufacture of lower olefins from oxygenates, is used for the manufacture of a hydroperoxide, i.e. tertiary butyl hydroperoxide, that is used for the epoxidation of lower olefins. In the epoxidation step, tertiary butanol is produced that may advantageously be recycled to oxygenate conversion step a). Under the conditions prevailing in the oxygenate conversion step a), tertiary butanol dehydrates into isobutene. Thus, iso-C4 hydrocarbons produced in the oxygenate conversion step are recycled as tertiary butanol to oxygenate conversion step a) and the loss of valuable iso-C4 hydrocarbons is minimized.

An advantage of the process according to the invention is that propylene oxide is formed as the only product. No major by-product, such as for example styrene in the SMPO process, is formed. A further advantage compared to an oxygenate-to-olefin step combined with the SMPO process, is that no additional feed stream (such as external benzene in a combined oxygenate-to-olefin/SMPO process) is needed.

BRIEF DESCRIPTION OF THE DRAWINGS

FIGS. 1 and 2 each schematically show a process according to the invention.

DETAILED DESCRIPTION OF THE INVENTION

Figure 1:
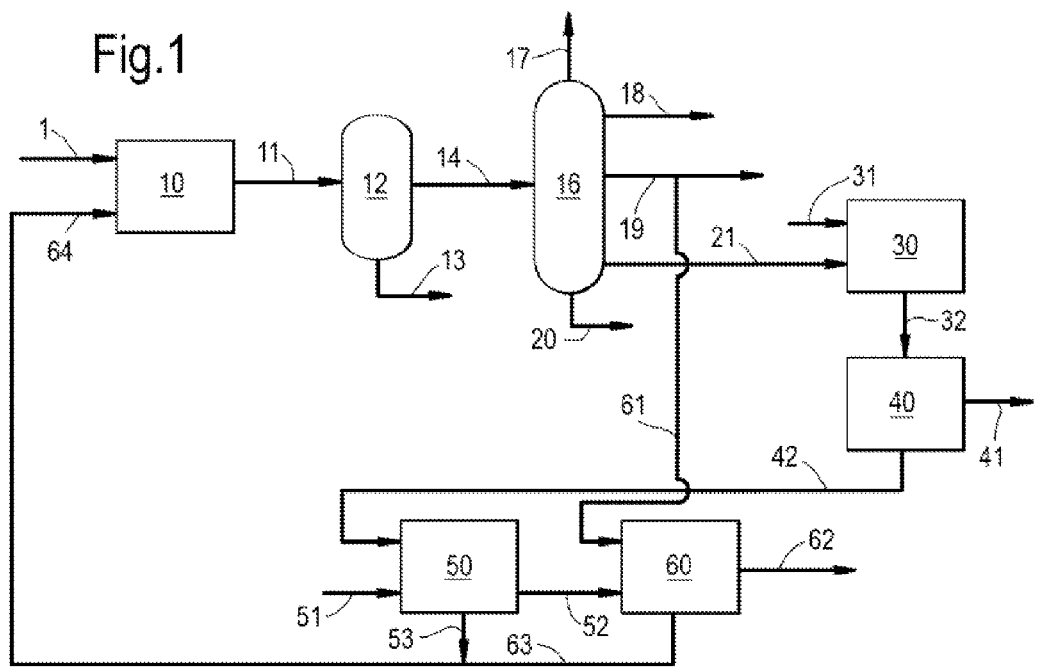

In the process according to the invention, an oxygenate is first converted into lower olefins by contacting the oxygenate with a molecular sieve-comprising catalyst at a temperature in the range of from 350 to 1000° C. (oxygenate conversion step a)). Besides lower olefins, i.e. ethylene and propylene, C4 olefinic and paraffinic hydrocarbons and, in a lesser amount C5+ olefinic and paraffinic hydrocarbons are formed as by-product. Thus, an olefinic product stream comprising ethylene, propylene, C4 hydrocarbons and higher hydrocarbons is obtained in step a). Typically, C4+ paraffins such as isobutane, n-butane, n-pentane, iso-pentane, and C4+ olefins such as isobutene, n-butenes, n-pentenes, iso-pentenes and C5+ naphtenes such as cyclopentane and cyclopentene will be present in the olefinic product stream. Small amounts of dienes like butadienes may be present in the olefinic product stream.

Reference herein to an oxygenate is to a compound comprising at least one alkyl group that is covalently linked to an oxygen atom. Preferably, at least one alkyl group has up to five carbon atoms, more preferably up to four, even more preferably one or two carbon atoms, most preferably at least one alkyl group is methyl. Mono-alcohols and dialkylethers are particularly suitable oxygenates. Methanol and dimethylether or mixtures thereof are examples of particularly preferred oxygenates.

The oxygenate conversion in step a) is carried out by contacting the oxygenate with a molecular sieve-comprising catalyst at a temperature in the range of from 350 to 1000° C., preferably of from 350 to 750° C., more preferably of from 450 to 700° C., even more preferably of from 500 to 650° C. The conversion may be carried out at any suitable pressure, preferably at a pressure in the range of from 1 bar to 50 bar (absolute), more preferably of from 1 bar to 15 bar (absolute). A pressure in the range of from 1.5 to 4.0 bar (absolute) is particularly preferred.

Any molecular sieve comprising catalyst known to be suitable for the conversion of oxygenates, in particular alkanols and dialkylethers, into lower olefins may be used. Preferably the catalyst comprises a molecular sieve having a 8-, 10- or 12-ring structure and an average pore size in the range of from 3 Å to 15 Å. Examples of suitable molecular sieves are silicoaluminophosphates (SAPOs), aluminophosphates (AlPO), metal-substituted aluminophosphates or metal-substituted silicoaluminophosphates. Preferred SAPOs include SAPO-5, -8, -11, -17, -18, -20, -31, -34, -35, -36, -37, -40, -41, -42, -44, -47 and -56. SAPO-17, -18, -34, -35, and -44 are particularly preferred.

A particular suitable class of molecular sieves are zeolites. In particular in case not only oxygenates but also C4+ olefins or compounds that form C4+ olefins under the reaction conditions prevailing in oxygenate conversion step a), e.g. a tertiary alcohol such as tertiary butanol or a tertiary alkylether such as methyl tertiary butylether, a zeolite-comprising catalyst is preferred as molecular-sieve comprising catalyst, more preferably a catalyst comprising a zeolite with a 10-membered ring structure. Zeolite-comprising catalysts are known for their ability to convert higher olefins to lower olefins, in particular C4+ olefins to ethylene and/or propylene. Suitable zeolite-comprising catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48. Preferably, the catalyst comprises at least one zeolite selected from MFI, MEL, TON and MTT type zeolites, more preferably at least one of ZSM-5, ZSM-11, ZSM-22 and ZSM-23 zeolites.

The zeolite in the oxygenate conversion catalyst is preferably predominantly in the hydrogen form. Preferably at least 50 wt %, more preferably at least 80 wt %, even more preferably at least 95 wt %, still more preferably at least 100 wt % of the zeolite is in the hydrogen form.

The molecular sieve-comprising catalyst may further comprise a binder material such as for example silica, alumina, silica-alumina, titania, or zirconia, a matrix material such as for example a clay, and/or a filler.

The oxygenate conversion catalyst may comprise phosphorous as such or in a compound, i.e. phosphorous other than any phosphorous included in the framework of the molecular sieve. It is preferred that an MEL or MFI-type zeolites comprising catalyst additionally comprises phosphorous. The phosphorous may be introduced by pre-treating the MEL or MFI-type zeolites prior to formulating the catalyst and/or by post-treating the formulated catalyst comprising the MEL or MFI-type zeolites. Preferably, a catalyst comprising MEL or MFI-type zeolites comprises phosphorous as such or in a compound in an elemental amount of from 0.05-10 wt % based on the weight of the formulated catalyst. A particularly preferred catalyst comprises phosphor-treated MEL or MFI-type zeolites having SAR of in the range of from 60 to 150, more preferably of from 80 to 100. An even more particularly preferred catalyst comprises phosphor-treated ZSM-5 having SAR of in the range of from 60 to 150, more preferably of from 80 to 100.

In step a), not only lower olefins and C4+ hydrocarbons, but also water is formed. Water is typically separated from the olefinic product stream by means known in the art, for example by cooling the effluent of step a) in a water quench tower.

In step b) of the process according to the invention, ethylene and/or propylene and a fraction comprising C4 hydrocarbons are separated from the olefinic product stream obtained in step a). Such separation in different fractions is done by means known in the art. Typically, the stream is fractionated in at least a fraction mainly comprising propylene and a fraction comprising C4 hydrocarbons. Usually, a fraction comprising mainly ethylene is first separated from the olefinic product stream in a de-ethaniser and a fraction mainly comprising propylene is then separated from the bottoms of the de-ethaniser in a de-propaniser. Instead of fractionating the olefinic product stream into separate ethylene and propylene fractions, a fraction comprising both ethylene and propylene may be obtained by directly supplying the olefinic product stream to a de-propaniser. The bottoms of the de-propaniser contain C4+ hydrocarbons. Preferably, the bottoms of the de-propaniser is further separated into a fraction mainly comprising C4 hydrocarbons and a fraction comprising C5+ hydrocarbons. In step c) at least part of the fraction comprising C4 hydrocarbons obtained in step b) is hydrogenated. This fraction comprising C4 hydrocarbons preferably is a fraction mainly comprising C4 hydrocarbons such a typically obtained from a de-butanizer tops. Alternatively, it may be a fraction comprising both C4 and higher hydrocarbons such as typically obtained from the bottoms of a de-propaniser.

The fraction comprising C4 hydrocarbons at least comprises normal butane, isobutane, normal butene and isobutene.

In step c), at least part of the fraction comprising C4 hydrocarbons is supplied to a hydrogenation zone and hydrogenated to saturate olefins present in the fraction. Thus, a saturated C4 hydrocarbon stream is obtained. The saturated C4 hydrocarbon stream will mainly comprise normal butane and isobutane. It may further comprise smaller amounts of normal pentanes, isopentanes and cyclopentane.

Hydrogenation is well-known in the art. Any catalyst and process conditions known to be suitable for hydrogenation of C4 olefins may be used. Suitable hydrogenation catalysts comprise a hydrogenating function, preferably a hydrogenating metal. The hydrogenation function is preferably a hydrogenating metal selected from Group VIII metals, more preferably selected from Pt, Pd, Ru, Rh, Ir, Ni and combinations thereof.

In step d), the saturated C4 hydrocarbon stream is separated into a steam enriched in normal butane and a stream enriched in isobutane. Such separation may be done by any separation means known to be suitable for normal/isobutane separation.

The stream enriched in normal butane may be withdrawn from the process and for example used for steam cracking, blended into an LPG pool, or isomerised to isobutane. Hydrogen produced in steam cracking of the stream enriched in normal butane can suitable be used in hydrogenation step c).

The isobutane in the stream enriched in isobutane is oxidized into tertiary butyl hydroperoxide. This is typically done by supplying the stream enriched in isobutane to an peroxidation unit wherein it is peroxidised with an oxidant, preferably air. Such peroxidation step is well-known in the art.

In step f), the tertiary butyl hydroperoxide obtained in step e) is reacted with ethylene and/or propylene separated from the olefinic product stream obtained in step a) to obtain the epoxide and tertiary butanol. Such epoxidation step is well-known in the art. Preferably, the tertiary butyl hydroperoxide is reacted with propylene to obtain propylene oxide.

In case propylene oxide is obtained in step f), the process according to the invention preferably further comprises converting the propylene oxide obtained in step f) into one or more polyether polyols, propylene glycol or propylene glycol ethers. Such conversion is known in the art and any suitable process conditions known in the art may be used. Polyether polyols can suitably be reacted with isocyanate to manufacture polyurethane.

The tertiary butanol obtained in step f) is preferably kept in the process by recycling it to step a). Under the reaction conditions prevailing in step a), tertiary butanol will be dehydrated and water and isobutene are formed. If the catalyst in step a) is able to catalyse conversion of isobutene into lower olefins, as is typically the case for a zeolite-comprising catalyst, in particular a catalyst comprising a zeolite with a 10-membered ring structure, part of the isobutene thus-formed will be further converted in lower olefins in step a).

Also in oxidation step e) tertiary butanol is produced as by-product. The tertiary butanol obtained in step e) may be recycled to step a), together with tertiary butanol from step f).

In order to maximize the propylene oxide yield of the process, it is, however, advantageous to keep a large part of the tertiary butanol formed in the process as an iso-C4 compound that can easily be converted into isobutene. Such isobutane can then be peroxidised to the tertiary butyl hydroperoxide that is needed for propylene oxide production in step f). Therefore, if the catalyst in step a) is able to convert isobutene into lower olefins, it is preferred to recycle at least part of the tertiary butanol formed in steps f) or in steps e) and f), after dehydration of the tertiary butanol to isobutene, to hydrogenation step c) or to a dedicated hydrogenation unit, for conversion into isobutane. The isobutane thus-formed is supplied to isobutane oxidation step e), either via normal/iso separation step d) or directly in case a dedicated hydrogenation unit was used.

More preferably, part of the tertiary butanol formed in step f) or in steps e) and f) is recycled to step a) and part is recycled, after dehydration and hydrogenation, as isobutane to step e). The recycling to step a) may be in the form of tertiary butanol or, after dehydration, in the form of isobutene.

In particular in case part of the tertiary butanol formed in step f) or in steps e) and f) is recycled as isobutane to step e), part of the fraction comprising C4 hydrocarbons obtained in step b) may be directly recycled to oxygenate conversion step a) instead of being supplied to the hydrogenation unit. In order to prevent a too high loss of iso-C4 compounds from the process, preferably at most 40%, more preferably at most 20%, even more preferably at most 10% of the fraction comprising C4 hydrocarbons is directly recycled to oxygenate conversion step a).

DETAILED DESCRIPTION OF THE DRAWINGS

In FIG. 1, an embodiment of the invention is schematically shown. Methanol is fed via line 1 to oxygenate conversion reaction zone 10 comprising an oxygenate conversion catalyst. In reaction zone 10, methanol is converted into olefins and water. Effluent from reaction zone 10 is supplied via line 11 to water quench tower 12 to be separated into water and an olefinic product stream. Water is withdrawn from tower 12 via line 13 and the olefinic product stream is supplied via line 14 to fractionation section 16. Fractionation section 16 comprises a de-ethaniser, a de-propaniser and a de-butaniser (not shown). The olefinic product stream is first fractionated by means of the deethaniser and depropaniser into an ethylene-rich stream, a propylene-rich stream, a C4+ hydrocarbon fraction and a lighter stream comprising light by-products such as methane and carbon oxides. The C4+ hydrocarbon fraction is further fractionated in the debutaniser into a C4 hydrocarbon fraction comprising isobutene and a fraction rich in C5+ hydrocarbons. The lighter stream, the ethylene-rich stream, the propylene-rich stream and the fraction rich in C5+ hydrocarbons are withdrawn from fractionation section 16 via lines 17, 18, 19 and 20, respectively. The fraction comprising C4 hydrocarbons is fed via line 21 to hydrogenation zone 30. Hydrogen is supplied via line 31 to reaction zone 30 comprising a hydrogenation catalyst. In hydrogenation zone 30, olefins present in the C4 hydrocarbon fraction are hydrogenated and a saturated C4 hydrocarbon stream is obtained. Saturated C4 hydrocarbon stream is supplied via line 32 to normal/iso separator 40 to be separated into a stream enriched in normal butane and a stream enriched in isobutane. The stream enriched in normal butane is withdrawn from the process via line 41 and may for example be supplied to a steam cracker furnace for the production of ethylene (not shown).

The stream enriched in isobutane obtained in separator 40 is supplied via line 42 to oxidation reaction zone 50. Air is supplied as oxidant to zone 50 via line 51. In zone 50, isobutane is oxidised to tertiary butyl hydroperoxide and tertiary butanol. The tertiary butyl hydroperoxide formed in zone 50 is supplied via line 52 to epoxidation zone 60. The tertiary butanol formed is withdrawn via line 53. Part of the propylene-rich stream separated in fractionation section 16 from the olefinic product stream is supplied to zone 60 via line 61. In zone 60, propylene oxide and tertiary butanol are formed. Propylene oxide is withdrawn as product via line 62. The tertiary butanol formed is withdrawn via line 63 and, combined with the tertiary butanol in line 53, recycled to oxygenate conversion zone 10 via line 64.

In FIG. 2, an alternative embodiment of the invention is schematically shown. Corresponding reference numbers have the same meaning as in FIG. 1. In the process as shown in FIG. 2, the combined tertiary butanol from lines 53 and 63 is supplied to dehydration zone 70, wherein tertiary butanol is dehydrated to form water and isobutene. Water is withdrawn via line 71, isobutene is withdrawn via line 72 and part of it is recycled via line 73 to hydrogenation zone 30 and part is recycled via line 74 to oxygenate conversion zone 10.

EXAMPLES

The invention is illustrated by the following non-limiting examples.

Example 1

Model calculations were carried out for a process configuration as shown in FIG. 1.

A stream of 3359 kilotons per annum (kton/a) of methanol, 150 kton/a of a recycle stream of tertiary butanol are supplied to oxygenate conversion zone 10. Zone 10 contains a zeolitic catalyst comprising ZSM23 and ZSM5 with a silica-to-alumina ratio of 280 in a weight ratio of 4 to 1. The effluent of zone 10 is supplied to water quench tower 12. In tower 12, the effluent is separated into 1889 kton/a of water is olefinic product stream. The olefinic product stream is fractionated in fractionation section 16. Fractionation yields 1051 kton/a of lower olefins, a C4 hydrocarbon fraction (277 kton/a) and a stream rich in C5+ hydrocarbons. The C4 hydrocarbon fraction and 9 kton/a of hydrogen are fed to hydrogenation zone 30 and a stream of 286 kton/a saturated C4 hydrocarbons is obtained. The saturated C4 hydrocarbons are separated in normal/iso separator 40 into 169 kton/a n-butane and 117 kton/a isobutane. The isobutane is oxidized with air in oxidation reaction zone 50 to obtain tertiary butyl hydroperoxide and tertiary butanol. The tertiary butyl hydroperoxide is reacted in epoxidation zone 60 with 43 kton/a propylene from fractionators 16 to obtain 59 kton/a propylene oxide. In zone 60, tertiary butanol is formed. Both the tertiary butanol formed in oxidation zone 50 and in epoxidation zone 60 is recycled to oxygenate conversion zone 10 (150 kton/a in total, which is equivalent to 113 kton/a of isobutene).

Example 2

Model calculations were carried out for a process configuration as in FIG. 2.

The amount of methanol fed to oxygenate conversion zone 10 is the same as in Example 1. In this configuration, more isobutene is fed to hydrogenation unit 30, due to the recycle of dehydrated tertiary butanol to unit 30. As a result, more isobutane is formed in zone 30. Thus, more tertiary butylhydroperoxide is available for conversion into propylene oxide in epoxidation zone 60.

In Table 1, the product streams in kilotons per day in the different lines with the reference numbers as in the Figure are given for EXAMPLE 1 and EXAMPLE 2.

TABLE 1

Product streams in kton/a in EXAMPLES 1 and 2

| line | Compound | EXAMPLE 1 | EXAMPLE 2 |
|---|---|---|---|
| 1 | methanol | 3359 | 3359 |
| 21 | C4 hydrocarbon fraction | 277 | 277 |
| 31 | hydrogen | 9 | 23 |
| 32 | saturated C4 hydrocarbons | 286 | 669 |
| 42 | isobutane | 117 | 500 |
| 61 | propylene | 43 | 181 |
| 62 | propylene oxide | 59 | 250 |
| 53 + 63 | tertiary butanol | 150 | 637 |
| 73 | isobutene | n.a. | 369 |
| 74 | isobutene | n.a. | 113 | n.a.: not applicable

Example 3

Co-Feeding Tertiary Butanol to Oxygenate-to-Olefins Conversion Step

This example illustrates that tertiary butanol recycled to an oxygenate conversion step a) comprising a catalyst comprising a zeolite with a 10-membered ring structure is converted into lower olefins.

Catalyst Preparation

Catalyst 1

A first catalyst (catalyst 1) was prepared as follows. ZSM-23 zeolite powder with a silica-to-alumina molar ratio (SAR) of 46, and ZSM-5 zeolite powder with a SAR of 80, both in the ammonium form, were mixed in a weight ratio of 1:1. Prior to mixing the powders, the ZSM-5 zeolite powder was treated with phosphorus. Phosphorus was deposited on the ZSM-5 zeolite powder by means of impregnation with an acidic solution containing phosphoric acid to obtain a phosphorous concentration of 2.0 wt %. The impregnated ZSM-5 powder was calcined at 550° C. The powder mixture was added to an aqueous solution to obtain a slurry and the slurry was milled. Kaolin clay and a silica sol were added to the milled slurry and the resulting mixture was spray-dried. The weight-based average particle size of the spray-dried powder was between 70 and 90 μm. The spray-dried catalyst was exposed to ion-exchange using an ammonium nitrate solution. Phosphorus was deposited on the spray-dried catalyst by means of impregnation using an acidic solution containing phosphoric acid. The concentration of the solution was adjusted to impregnate 1.0 wt % of phosphorus on the catalyst. After impregnation the catalyst was dried at 140° C. and calcined at 550° C. for 2 hours. The catalyst thus obtained (40 wt % zeolite, 36 wt % kaolin clay and 24 wt % silica) is further referred to as catalyst 1.

Catalyst 2

A second catalyst (catalyst 2) was prepared as described hereinabove for catalyst 1, except that as zeolite powder only ZSM-5 with a SAR of 80 which was not treated with phosphorus prior to spray-drying, was used. After spray-drying, the concentration of the phosphorus impregnation solution was adjusted to impregnate 1.5 wt % of phosphorus on the spray-dried catalyst formulation. The final formulated catalyst thus obtained is further referred to as catalyst 2.

Oxygenate to Olefin Conversion

The conversion of tertiary butanol into olefins was tested by feeding different feed compositions with and without tertiary butanol to an oxygenate conversion catalyst (the tertiary butanol containing 20 wt % of isobutanol in order to make feeding as a liquid at room temperature possible). Three different feed compositions were used:

3 vol % tertiary butanol, balance $N_2$;

3 vol % tertiary butanol, 6 vol % methanol, balance $N_2$;

3 vol % 1-butene, 6 vol % methanol, balance $N_2$.

Each feed composition was tested over two different catalysts (catalysts 1 and 2) and at two different reaction temperatures (525 and 575° C.).

The experiments were carried out as follows. A sieve fraction of 60-80 mesh of catalyst was used, which was treated ex-situ in air at 550° C. for 2 hours. The catalyst was placed in a quartz reactor tube of 1.8 mm internal diameter. The catalyst was then heated under a flow of nitrogen to the reaction temperature and subsequently the feed composition was passed over the catalyst at atmospheric pressure (1 bar atmosphere). The gas hourly space velocity (GHSV), i.e. the total gas flow per gram of zeolite per hour, was 19,000 (ml.g zeolite$^{-1}$.h$^{-1}$). The effluent from the reactor was analyzed by gas chromatography (GC) to determine which products were formed. The effluent composition was calculated by the quotient of the mass of a specific product by the total mass of hydrocarbon products in the effluent. The results are shown in Table 2.

TABLE 2

Experiments performed with tertiary butanol

| Catalyst | Feed | T (° C.) | C2= (wt %) | C3= (wt %) | C4 (wt %) | C5 (wt %) | C6+ (wt %) | Light ends (wt %) | C4 sat/C4 total (wt/wt) |
|---|---|---|---|---|---|---|---|---|---|
| 1 | tC4OH | 575 | 7.42 | 19.98 | 68.13 | 3.01 | 1.24 | 0.22 | 1.43 |
| 1 | tC4OH/MeOH | 575 | 17.02 | 50.71 | 26.38 | 2.17 | 3.15 | 0.57 | 3.77 |
| 1 | C4=/MeOH | 575 | 17.54 | 52.08 | 25.38 | 1.80 | 2.58 | 0.61 | 2.23 |
| 2 | tC4OH | 575 | 12.15 | 30.85 | 51.86 | 2.28 | 2.54 | 0.32 | 2.73 |
| 2 | tC4OH/MeOH | 575 | 19.59 | 49.61 | 22.94 | 1.96 | 5.00 | 0.91 | 7.74 |
| 2 | C4=/MeOH | 575 | 20.76 | 50.88 | 21.45 | 1.87 | 4.32 | 0.72 | 4.42 |
| 1 | tC4OH | 525 | 7.64 | 28.32 | 55.58 | 5.92 | 2.49 | 0.06 | 2.59 |
| 1 | tC4OH/MeOH | 525 | 13.79 | 48.93 | 27.89 | 4.20 | 4.93 | 0.27 | 5.61 |
| 1 | C4=/MeOH | 525 | 14.28 | 51.47 | 26.30 | 3.32 | 4.39 | 0.23 | 3.37 |
| 2 | tC4OH | 525 | 12.26 | 39.47 | 40.85 | 3.84 | 3.35 | 0.23 | 4.31 |
| 2 | tC4OH/MeOH | 525 | 16.83 | 48.48 | 24.45 | 3.41 | 6.28 | 0.54 | 8.05 |
| 2 | C4=/MeOH | 525 | 17.04 | 50.45 | 23.85 | 3.21 | 5.15 | 0.31 | 5.25 | tC4OH: tertiary butanol;
C4=: 1-butene;
C2=: ethylene;
C3=: propylene;
C4 sat: saturated C4 hydrocarbons.

From the results shown in Table 2, it can be concluded that recycling of tertiary butanol to a 10-membered ring zeolite catalyst under oxygenate conversion conditions results in conversion of the tertiary butanol into lower olefins. The above experiments were repeated, except that isobutanol was used instead of tertiary butanol. The results are shown in Table 3.

TABLE 3

Experiments performed with isobutanol

| Catalyst | Feed | T (° C.) | C2= (wt %) | C3= (wt %) | C4 total (wt %) | C5 total (wt %) | C6+ (wt %) | Light ends (wt %) | C4 sat/C4 total (wt/wt) |
|---|---|---|---|---|---|---|---|---|---|
| 1 | iC4OH | 575 | 8.37 | 22.81 | 64.73 | 2.86 | 1.15 | 0.09 | 1.36 |
| 1 | iC4OH/MeOH | 575 | 17.07 | 50.97 | 27.62 | 2.02 | 2.15 | 0.17 | 2.39 |
| 1 | C4=/MeOH | 575 | 16.07 | 52.81 | 26.81 | 1.95 | 2.06 | 0.29 | 1.72 |
| 2 | iC4OH | 575 | 12.91 | 32.65 | 49.65 | 2.05 | 2.48 | 0.25 | 3.01 |
| 2 | iC4OH/MeOH | 575 | 19.56 | 50.53 | 23.91 | 1.74 | 3.70 | 0.55 | 4.09 |
| 2 | C4=/MeOH | 575 | 18.16 | 51.93 | 23.62 | 1.63 | 3.88 | 0.77 | 2.64 |
| 1 | iC4OH | 525 | 8.30 | 30.58 | 52.70 | 5.64 | 2.75 | 0.03 | 2.72 |
| 1 | iC4OH/MeOH | 525 | 13.73 | 49.31 | 28.41 | 4.08 | 4.41 | 0.05 | 4.24 |
| 1 | C4=/MeOH | 525 | 13.16 | 50.98 | 27.91 | 3.97 | 3.95 | 0.04 | 2.93 |
| 2 | iC4OH | 525 | 13.16 | 41.77 | 37.70 | 3.62 | 3.57 | 0.17 | 5.08 |
| 2 | iC4OH/MeOH | 525 | 16.76 | 49.29 | 24.70 | 3.33 | 5.53 | 0.39 | 5.77 |
| 2 | C4=/MeOH | 525 | 15.94 | 50.68 | 24.54 | 3.11 | 5.15 | 0.58 | 4.09 | iC4OH: isobutanol;
C4=: 1-butene;
C2=: ethylene;
C3=: propylene;
C4 sat: saturated C4 hydrocarbons.

It can be seen by comparing Tables 2 and 3 that the results with isobutanol are comparable with the results with tertiary butanol. Also the results with 1-butene (C4=in Tables 2 and 3) are comparable with those with tertiary butanol or isobutanol. This indicates that the conversion of tertiary butanol in an oxygenate-to-olefins conversion step a) over a zeolitic catalyst goes via the conversion into isobutene and that isomerisation between isobutene and 1-butane occurs.

What is claimed is:

1. A process for preparing an epoxide from an oxygenate, the process comprising the following steps:
   a) contacting the oxygenate with a molecular sieve-comprising catalyst, at a temperature in the range of from 350 to 1000° C. to obtain an olefinic product stream comprising ethylene, propylene and C4 hydrocarbons;
   b) separating ethylene and/or propylene and a fraction comprising C4 hydrocarbons including normal butane, isobutane, normal butene and isobutene, from the olefinic product stream;
   c) hydrogenating at least part of the fraction comprising C4 hydrocarbons in a hydrogenation unit to obtain a saturated C4 hydrocarbon stream;
   d) separating the saturated C4 hydrocarbon stream into a stream enriched in normal butane and a stream enriched in isobutane;
   e) oxidizing the isobutane in the stream enriched in isobutane into tertiary butyl hydroperoxide; and
   f) reacting tertiary butyl hydroperoxide obtained in step d) with ethylene and/or propylene separated from the olefinic product stream obtained in step a) to obtain the epoxide and tertiary butanol.

2. A process according to claim 1, wherein the molecular sieve-containing catalyst is a zeolite-comprising catalyst.

3. A process according to claim 2, wherein the zeolite-comprising catalyst comprises at least one zeolite selected from MFI, MEL, TON and MTT zeolites.

4. A process according to claim 3, wherein the zeolite-comprising catalyst comprises at least one of ZSM-5, ZSM-11, ZSM-22 and ZSM-23 zeolites.

5. A process according to claim 1, wherein the oxygenate is selected from the group consisting of alkanols and di-alkylethers having up to five carbon atoms.

6. A process according to claim 5, where the oxygenate is methanol, dimethylether, or a mixture thereof.

7. A process according to claim 1, further comprising the following step:
  g) recycling at least part of the tertiary butanol obtained in step f) to step a).

8. A process according to claim 7, wherein tertiary butanol is co-produced in step e) and wherein tertiary butanol produced in step e) is recycled to step a).

9. A process according to claim 7, wherein the tertiary butanol recycled to step a) is dehydrated prior to recycling to step a).

10. A process according to claim 8, wherein the tertiary butanol recycled to step a) is dehydrated prior to recycling to step a).

11. A process according to claim 1, wherein at least part of the tertiary butanol obtained in step f) is first dehydrated and then hydrogenated to obtain isobutane and wherein the isobutane thus-obtained is recycled to step e).

12. A process according to claim 11, wherein the dehydrated tertiary butanol is hydrogenated by supplying the dehydrated tertiary butanol to hydrogenation step c).

13. A process according to claim 1, wherein a part of the fraction comprising C4 hydrocarbons obtained in step b) is recycled directly to step a).

\* \* \* \* \*